(12) United States Patent
Corndorf et al.

(10) Patent No.: US 9,345,892 B2
(45) Date of Patent: May 24, 2016

(54) TRANSCEIVER DUTY CYCLED OPERATIONAL MODE

(75) Inventors: Eric D. Corndorf, Minneapolis, MN (US); Gary P. Kivi, Maple Grove, MN (US); Matthew D. Kirkwood, St. Paul, MN (US); Nicholas C. Wine, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 2247 days.

(21) Appl. No.: 12/363,109

(22) Filed: Jan. 30, 2009

(65) Prior Publication Data

US 2010/0198280 A1   Aug. 5, 2010

(51) Int. Cl.
  *A61N 1/08*    (2006.01)
  *A61N 1/372*   (2006.01)
  *G06F 19/00*   (2011.01)

(52) U.S. Cl.
  CPC ........ *A61N 1/37276* (2013.01); *G06F 19/3406* (2013.01); *G06F 19/3418* (2013.01)

(58) Field of Classification Search
  CPC .................................................. A61N 1/37276
  USPC ...................................................... 607/32, 60
  See application file for complete search history.

(56) References Cited

U.S. PATENT DOCUMENTS

| | | | |
|---|---|---|---|
| 4,835,372 A | 5/1989 | Gombrich et al. | |
| 5,342,408 A * | 8/1994 | deCoriolis et al. | ............... 607/32 |
| 5,350,411 A | 9/1994 | Ryan et al. | |
| 5,476,488 A | 12/1995 | Morgan et al. | |
| 6,185,452 B1 | 2/2001 | Schulman et al. | |
| 6,411,064 B1 | 6/2002 | Brink | |
| 6,472,991 B1 * | 10/2002 | Schulman et al. | ......... 340/995.1 |
| 6,501,978 B2 | 12/2002 | Wagshul et al. | |
| 6,701,188 B2 | 3/2004 | Stroebel et al. | |
| 7,162,307 B2 | 1/2007 | Patrias | |

(Continued)

FOREIGN PATENT DOCUMENTS

| WO | WO 03053515 | 7/2003 |
|---|---|---|
| WO | WO 2005099816 | 10/2005 |

OTHER PUBLICATIONS

International Search Report, PCT/US2009/036602, 4 pages.

(Continued)

*Primary Examiner* — Allen Porter, Jr.
(74) *Attorney, Agent, or Firm* — Michael J. Ostrom

(57) ABSTRACT

This disclosure describes an operational mode of a telemetry module. A device, such as a programming device, operating in accordance with the techniques of this disclosure determines that a transceiver of an implantable medical device is operating in a duty cycled operational mode that includes at least one interval during which the transceiver is powered down interleaved with intervals during which the transceiver is powered up, e.g., for transmitting or receiving communications over an established communication session. The programming device is configured to transmit information during the at least one interval in which the transceiver of the implantable medical device is powered down. Doing so ensures that the channel over which the programmer and implantable medical device communicate will not be usurped by another device.

33 Claims, 7 Drawing Sheets

(56) References Cited

U.S. PATENT DOCUMENTS

| | | | |
|---|---|---|---|
| 2003/0045913 A1 | 3/2003 | Stroebel et al. | |
| 2003/0149459 A1 | 8/2003 | Von Arx et al. | |
| 2005/0010269 A1 | 1/2005 | Lebel et al. | |
| 2005/0240245 A1 | 10/2005 | Bange et al. | |
| 2006/0047367 A1 | 3/2006 | Rogers et al. | |
| 2006/0115016 A1 | 6/2006 | Chen et al. | |
| 2006/0247736 A1* | 11/2006 | Roberts ........................... | 607/60 |
| 2007/0083246 A1 | 4/2007 | Mazar et al. | |
| 2007/0123946 A1 | 5/2007 | Masoud | |
| 2007/0150028 A1 | 6/2007 | Parkinson et al. | |

OTHER PUBLICATIONS

International Search Report, PCT/US2009/036644, 4 pages.

Sagan, Didier, RF Integrated Circuits for Medical Applications: Meeting the Challenge of Ultra Low Power Communication, pp. 1-2, downloaded Nov. 24, 2008 from http://stf.ucsd.edu/presentations/2007-08%20STF%20-%20abstract%20RF%20IC%20for%20Medical%20Apps%20-%20Meeting%20the%20Challenge%20of%20ULP%20Communications.pdf.

Zarlink Semiconductor, ZL70101 Medical Implant RF Transceiver Data Sheet, May 2007, pp. 1-8.

\* cited by examiner

TRANSCEIVER DUTY CYCLED OPERATIONAL MODE

TECHNICAL FIELD

The disclosure relates generally to implantable medical devices and, in particular, to telemetry communication between an implantable medical device and another device.

BACKGROUND

A wide variety of implantable medical devices (IMDs) that deliver a therapy or monitor a physiologic condition of a patient have been clinically implanted or proposed for clinical implantation in patients. IMDs may include a therapy module that delivers therapy or monitors conditions with respect to a variety of organs, nerves, muscles or tissues of the patients, such as the heart, brain, stomach, spinal cord, pelvic floor, or the like. In some cases, IMDs may deliver electrical stimulation therapy via one or more electrodes, which may be included as part of one or more elongated implantable medical leads.

For example, an implantable cardiac device, such as a cardiac pacemaker or implantable cardioverter-defibrillator, provides therapeutic stimulation to the heart by delivering electrical therapy signals such as pulses or shocks for pacing, cardiac resynchronization, cardioversion, or defibrillation via electrodes of one or more implantable leads. As another example, a neurostimulator may deliver electrical therapy signals, such as pulses, to a spinal cord, brain, pelvic floor or the like to alleviate pain or treat symptoms of any of a number of neurological or other diseases, such as epilepsy, gastroparesis, Alzheimer's, depression, obesity, incontinence and the like.

IMDs may also deliver, in addition to or instead of electrical stimulation therapy, drug therapy. For example, the IMD may deliver a drug or other therapeutic agent to the patient to treat pain or other symptoms of the condition of the patient. For example, the IMD may deliver morphine to an intrathecal location to treat pain. As another example, the IMD may deliver chemotherapy for the treatment of cancer. An IMD that delivers a drug or other therapeutic agent may sometimes be referred to as a drug pump or drug delivery device.

IMDs may include a telemetry module that may exchange communications with a programming device (sometimes referred to as a programmer). For example, the IMDs may transmit information related to a condition of a patient, such as physiological signals measured by one or more sensors, or information related to a therapy delivered to the patient. This information may be previously stored or real-time information. The IMDs may also receive information from the programmer, such as configuration information that may be used to configure a therapy to be provided to the patient.

The various components of the IMDs, including the therapy module and the telemetry module, receive power from a power source. The power source may, in some instances, be a battery that has a limited service life. The service life of the battery may vary greatly based on the type of therapy provided to the patient. The service life of the battery, however, is typically on the order of several to tens of years.

SUMMARY

This disclosure relates to operational modes of a telemetry module. A device, such as a programming device, operating in accordance with the techniques of this disclosure determines that a transceiver of an implantable medical device is operating in a duty cycled operational mode that includes at least one interval during which the transceiver is powered down interleaved with intervals during which the transceiver is powered up, e.g., for transmitting or receiving communications over an established communication session. The programming device is configured to transmit information during the at least one interval in which the transceiver of the implantable medical device is powered down. Doing so ensures that the channel over which the programmer and implantable medical device communicate will not be usurped by another device.

In one example, this disclosure is directed to a system that includes an implantable medical device and a programming device that communicates with the implantable medical device. The implantable medical device includes a telemetry module configured to operate in a duty cycled operational mode that includes at least one interval during which a transceiver of the telemetry module is powered down interleaved with intervals during which the transceiver is powered up for transmitting or receiving communications over an established communication session. The telemetry module maintains information regarding the established communication session during the at least one interval in which the transceiver is powered down. The programming device transmits information during the at least one period in which the transceiver is powered down.

In another example, this disclosure is directed to a programming device comprising a telemetry module that exchanges communications with an implantable medical device and a processor that controls operation of the telemetry module. The processor determines that a transceiver of the implantable medical device is operating in a duty cycled operational mode that includes at least one interval during which a transceiver of the telemetry module is powered down interleaved with intervals during which the transceiver is powered up for transmitting or receiving communications over an established communication session and controls the telemetry module to transmit information during the at least one interval in which the transceiver of the implantable medical device is powered down.

In another example, this disclosure is directed to a method comprising determining that a transceiver of an implantable medical device is operating in a duty cycled operational mode that includes at least one interval during which the transceiver is powered down interleaved with intervals during which the transceiver is powered up for transmitting or receiving communications over an established communication session and transmitting information during the at least one interval in which the transceiver of the implantable medical device is powered down.

In another example, this disclosure is directed to a device comprising means for determining that a transceiver of an implantable medical device is operating in a duty cycled operational mode that includes at least one interval during which the transceiver is powered down interleaved with intervals during which the transceiver is powered up for transmitting or receiving communications over an established communication session and means for transmitting information during the at least one interval in which the transceiver of the implantable medical device is powered down.

In another example, this disclosure is directed to a computer-readable medium comprising instructions that when executed cause a device to determine that a transceiver of an implantable medical device is operating in a duty cycled operational mode that includes at least one interval during which the transceiver is powered down interleaved with intervals during which the transceiver is powered up for transmitting or receiving communications over an established communication session and transmit information during the at least one interval in which the transceiver of the implantable medical device is powered down.

This summary is intended to provide an overview of the subject matter described in this disclosure. It is not intended to provide an exclusive or exhaustive explanation of the techniques described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
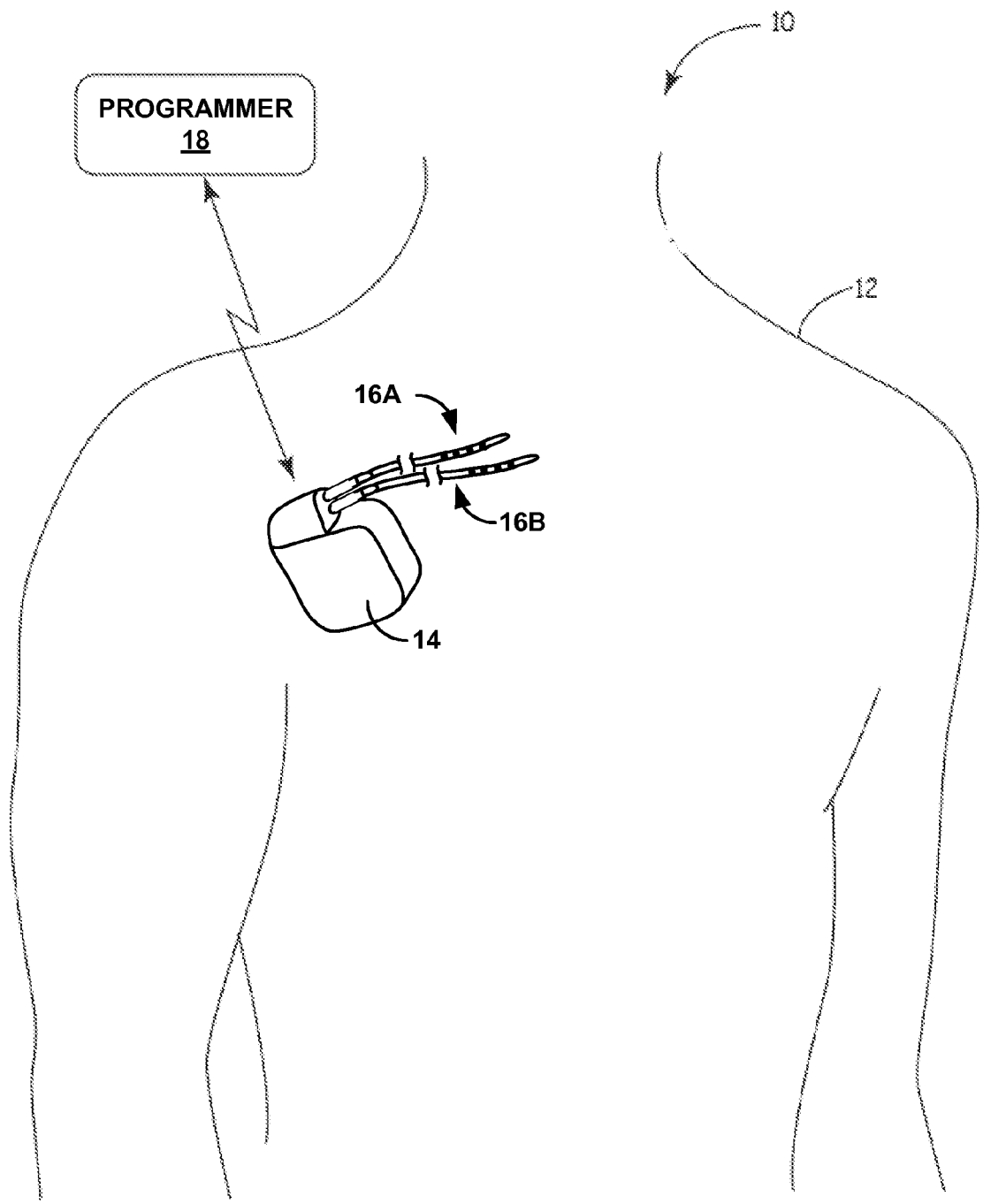
FIG. 1 is a conceptual diagram illustrating an example therapy system that may be used to provide therapy to a patient.

FIG. 1 is a conceptual diagram illustrating an example therapy system 10 that may be used to provide therapy to a patient 12. Patient 12 ordinarily, but not necessarily, will be a human. Therapy system 10 includes an IMD 14 and elongated members 16A and 16B (collectively, "elongated members 16") that extend from IMD 14. Therapy system 10 may also include a programming device, such as programmer 18, that is wirelessly coupled to IMD 14.

IMD 14 may be any of a variety of therapy devices. For example, IMD 14 may be a device that provides electrical stimulation therapy. As such, elongated members 16 may be implantable leads with one or more electrodes (not shown) for delivering therapy to and/or sensing a physiological parameter of patient 12. Elongated members 16 may be coupled to IMD 14 via a connector block. In particular, proximal ends of elongated members 16 may include electrical contacts that electrically couple to respective electrical contacts within the connector block of IMD 14. In addition, in some examples, elongated members 16 may be mechanically coupled to the connector block of IMD 14 with the aid of set screws, connection pins or another suitable mechanical coupling mechanism. The configuration of therapy system 10 illustrated in FIG. 1 is merely an example. In other examples, an IMD 14 may be coupled to more than two elongated members 16, or may be coupled to a single elongated member 16.

Each of the elongated members 16 may include an insulative lead body, which may carry a number of concentric coiled conductors separated from one another by tubular insulative sheaths. Other lead configurations are also contemplated, such as lead configurations that do not include coiled conductors. Elongated members 16 may include one or more electrodes that are located proximate to a distal end of elongated member 16 (not shown). The one or more electrodes may include ring electrodes, extendable helix tip electrodes, coil electrodes, or any other type of electrode or a combination of different types of electrodes. Each of the electrodes may be electrically coupled to a respective one of the conductors within the lead body of its associated elongated member 16. In some instances, a housing of IMD 14 or a sensor located on IMD 14 may also function as an electrode for sensing or therapy delivery.

In some instances, IMD 14 may be a device that provides electrical stimulation therapy in the form of cardiac rhythm management therapy to a heart of patient 12 via elongated members 16. As such, elongated members 16 may be implanted within one or more atria or ventricles of the heart of patient 12 or a combination thereof. In other words, IMD 14 may be used for single chamber or multi-chamber cardiac rhythm management therapy. The cardiac rhythm management therapy delivered by IMD 14 may include, for example, pacing, cardioversion, defibrillation and/or cardiac resynchronization therapy (CRT). In some examples, IMD 14 may deliver pacing pulses, but not cardioversion or defibrillation shocks, while in other examples, IMD 14 may deliver cardioversion or defibrillation shocks, but not pacing pulses. In addition, in further examples, IMD 14 may deliver pacing pulses, cardioversion shocks, and defibrillation shocks. As such, IMD 14 may operate as an implantable pacemaker, cardioverter, and/or defibrillator.

In other instances, IMD 14 may be a device that provides electrical stimulation to a non-myocardial tissue site of patient 12. As such, elongated members may be implanted to provide stimulation to a tissue proximate a vagus nerve, a spinal cord, brain, stomach, pelvic floor, or the like. IMD 14 delivers the electrical stimulation to the non-myocardial tissues site via one or more of elongated members 16. Thus, as in the case of cardiac therapy, elongated members 16 may be leads that include one or more electrodes for delivery therapy to and/or sensing of a physiological parameter of patient 12. A non-myocardial tissue site may include a tissue site that does not include cardiac muscle (e.g., the myocardium). For example, a non-myocardial tissue site may be proximate a muscle other than cardiac muscle, an organ other than the heart, or neural tissue. The non-myocardial tissue site may include extravascular tissue sites or intravascular tissue sites.

In addition to providing electrical stimulation therapy, IMD 14 may sense one or more physiological parameters of patient 12. When elongated members 16 are implanted within the heart of patient 12, the electrodes proximate the distal end of elongated members 16 may sense electrical signals attendant to the depolarization and repolarization of the heart. IMD 14 may analyze the sensed signals to monitor a rhythm of the heart or detect particular heart conditions, e.g., tachycardia, bradycardia, fibrillation or the like. IMD 14 may sense a variety of other physiologic parameters or other parameters related to a condition of patient 12, including, for example, neurologic parameters, intracardiac or intravascular pressure, activity, posture, pH of blood or other bodily fluids or the like. As such, IMD 14 may be a wireless sensor.

A user, such as a physician, technician, or other clinician, may interact with programmer 18 to communicate with IMD 14. For example, the user may interact with programmer 18 to retrieve physiological or diagnostic information from IMD 14. For example, the user may use programmer 18 to retrieve information from IMD 14 regarding the rhythm of the heart of patient 12, trends therein over time, or cardiac arrhythmia episodes. As another example, the user may use programmer 18 to retrieve information from IMD 14 regarding other sensed physiological parameters of patient 12, such as electrical depolarization/repolarization signals from the heart (referred to as "electrogram" or EGM), intracardiac or intravascular pressure, activity, posture, respiration or thoracic impedance. As another example, the user may use programmer 18 to retrieve information from IMD 14 regarding the performance or integrity of IMD 14 or other components of system 10, such as leads or a power source of IMD 14.

The user may also interact with programmer 18 to program IMD 14, e.g., select values for operational parameters of IMD 14. For electrical stimulation therapies, for example, the user may interact with programmer 18 to program a therapy progression, select an electrode or combination of electrodes of elongated members 16 to use for delivering electrical stimulation (pulses or shocks), select parameters for the electrical pulse or shock (e.g., pulse amplitude, pulse width, or pulse rate), select electrodes or sensors for use in detecting a physiological parameter of patient 12, or the like. By programming these parameters, the physician or other user can attempt to generate an efficacious therapy for patient 12 that is delivered via the selected electrodes.

Programmer 18 may be a dedicated hardware device with dedicated software for programming of IMD 14. Alternatively, programmer 18 may be an off-the-shelf computing device running an application that enables programmer 18 to program IMD 14. In some examples, programmer 18 may be a handheld computing device or a computer workstation. Programmer 18 may, in some instances, include a programming head that may be placed proximate to the patient's body near the implant site of IMD 14 in order to improve the quality or security of communication between IMD 14 and programmer 18. Programmer 18 may include a user interface that receives input from the user and/or displays data to the user.

Programmer 18 may communicate with IMD 14 via wireless communication using any techniques known in the art. Examples of communication techniques may include, for example, low frequency or radiofrequency (RF) telemetry, but other techniques are also contemplated. In some instances, programmer 18 and IMD 14 may communicate in the 402-405 MHz frequency band in accordance with the Medical Implant Communications Service (MICS) band regulations. In accordance with the MICS band regulations, the frequency band is divided into a plurality of channels, e.g., ten channels with each channel having a 300 KHz sub-band. The MICS protocol may require that a device desiring to use the MICS band "listen" to the channels to before selecting a channel to ensure that an unused MICS channel is selected. In other instances, programmer 18 and IMD 14 may communicate over the 401-402 MHz or 405-406 MHz frequency bands in accordance with the Medical External Data Service (MEDS) band regulations. In other words, the MEDS band is a split channel band, i.e., occupies frequency bands that are divided by the MICS band.

The power demands of a telemetry module of IMD 14 during wireless communication with programmer 18 may obstruct, impede or otherwise interfere with the ability of IMD 14 to perform other power intensive tasks, such as delivering therapies to patient 12. For example, the combined power demands of the telemetry module and another component, such as a therapy module, of IMD 14 may draw current at a high rate from a power source, e.g., battery, of IMD 14. The current drawn from the battery causes a voltage to drop due to an impedance of the battery. As the impedance of the battery increases with battery age, the voltage drop during the high rate of current draw may be significant enough to render the battery incapable of supplying current at a desired rate. The telemetry module of IMD 14 may operate in accordance with the techniques of this disclosure to free up the power source for non-telemetry functions, such as the therapy delivery functions, thereby decreasing the current demands.

As will be described in further detail below, the telemetry module of IMD 14 may detect a telemetry configuration event and configure the telemetry module to operate in a "duty cycled operational mode" in which one or more intervals during which a transceiver of the telemetry module is powered down are interleaved with intervals during which the transceiver is powered up for transmitting and/or receiving communications over an established communication session or channel. The powered down state may refer to a "sleep" state or other low power state in which the current drawn from the power source is substantially less than the current drawn from the power source in the powered up state. Therefore, the telemetry module may still draw current from the power source in the powered down state, albeit at a lower rate than the powered up state.

The duty cycled operational mode may enable other components, such as the therapy module, to draw current from the power source during the intervals in which the transceiver is powered down. In this manner, IMD 14 may be perceived as multiplexing the use of the power source among the various components during periods in which the rate at which current is drawn from the power source is greatest. In contrast, when operating in a "normal operational mode," the telemetry module of IMD 14 has no intervals during which the transceiver is powered down. Instead, the various components utilize the power source concurrently, resulting in a high rate of current draw from power source.

Although the techniques of this disclosure are described primarily with respect to power demands of multiple components operating concurrently, the duty cycling techniques of this disclosure may be used other contexts in which there is no competition for the resources of the power source of IMD 14. For example, the telemetry module of IMD 14 may operate in accordance with the techniques of this disclosure in response to detecting that IMD 14 is nearing end-of-service, thus reducing average current demands on the power source when IMD 14 is nearing end-of-service. As another example, the telemetry module of IMD 14 may obtain power from a hold capacitor that hands off a battery and operate in accordance with the techniques of this disclosure to allow the capacitor to recharge. As a further example, the telemetry module of IMD 14 may operate in accordance with the techniques of this disclosure to allow an energy harvesting device to harvest bursts of energy.

During the intervals in which the transceiver is powered down, the telemetry module may maintain information regarding the established communication session such that transmit and receive operations may immediately begin once the next interval during which the transceiver is powered up begins. In some instances, programmer 18 may continue to transmit information during the intervals in which the transceiver of the telemetry module is powered down in order to prevent another device from usurping the channel over which the communication session is established.

Although FIG. 1 is described in the context of providing therapy to patient 12, the techniques of this disclosure may be used in IMDs that do not provide therapy to a patient. As one example, the techniques of this disclosure may be used in an IMD that only provides monitoring of patient 12, such as an implantable loop recorder.

Figure 2:
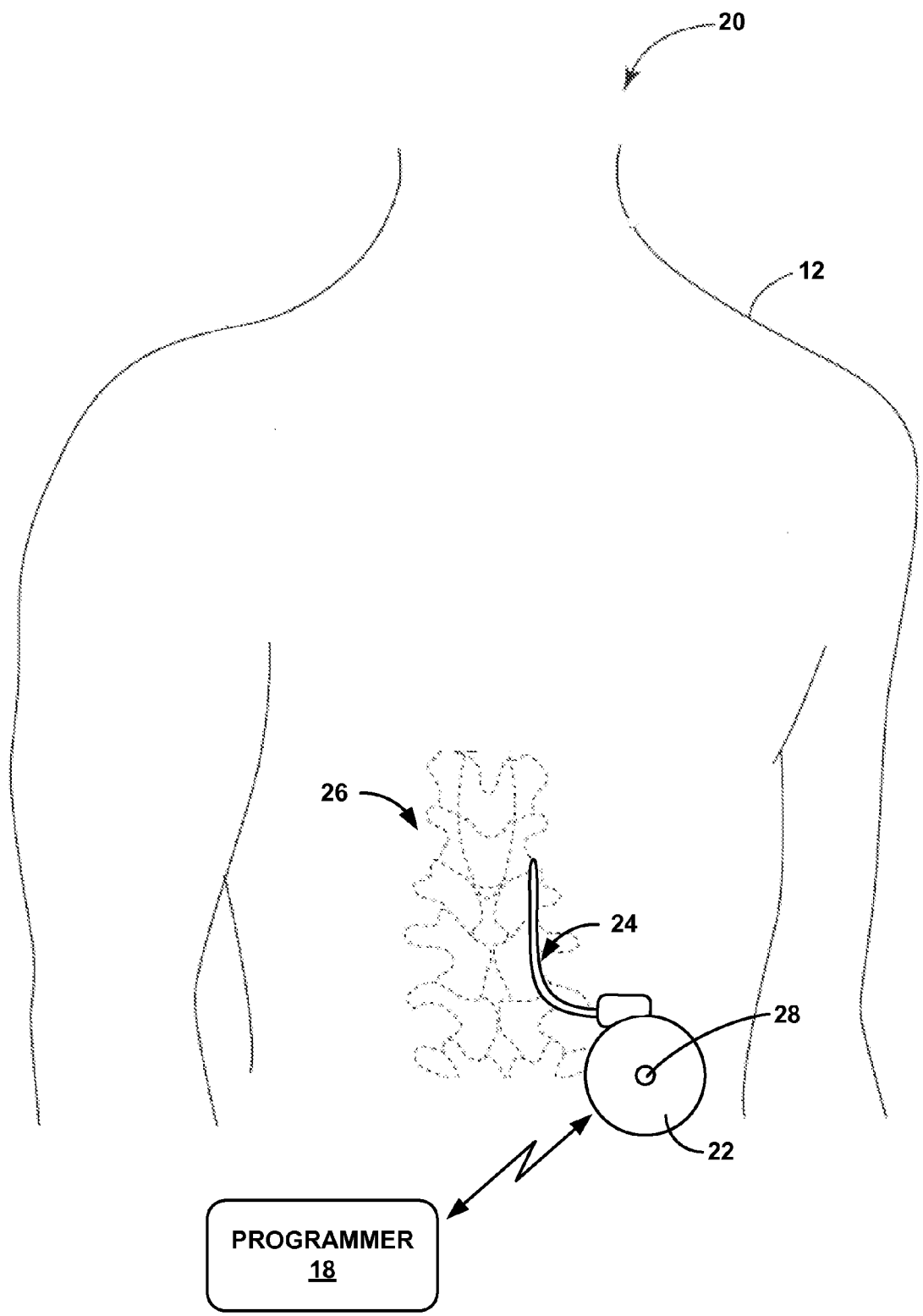
FIG. 2 is a conceptual diagram illustrating another example therapy system that may be used to provide therapy to a patient.

FIG. 2 is a conceptual diagram illustrating another example therapy system 20 that may be used to provide therapy to a patient 12. Therapy system 20 includes an IMD 22 and an elongated member 24 that extends from IMD 22. Therapy system 10 may also include a programmer 18 that is wirelessly coupled to IMD 22. Programmer 18 may operate in a similar manner as that described above with respect to FIG. 1.

IMD 22 may be a device that delivers a drug or therapeutic agent to patient 12 via elongated member 24. Thus, elongated member 24 may be a catheter for delivery of the drug or therapeutic agent to a specific location within patient 12, sometimes referred to as a drug delivery site. IMD 22 may, for example, be implanted within a subcutaneous pocket in an abdomen of patient 12. Elongated member 24 (e.g., catheter) may be implanted within patient 12 and extend from IMD 22 into the intrathecal space of spine 26. IMD 22 may be implanted in locations other than the abdomen, such as in a location near a shoulder or location near an upper buttock of patient 12. Likewise, elongated member 24 may be implanted in different locations depending on the application, such as within a stomach, pelvic floor or brain of patient 12.

In the example illustrated in FIG. 2, IMD 22 delivers the drug or therapeutic agent via a single catheter. In some instances, however, more than one catheter may be used to deliver the same drug or therapeutic agent to a second location within patient 12. In other instances, more than one catheter may be used to deliver a different drug or therapeutic agent to the same or different location.

When operating as a drug pump or a drug delivery device, IMD 22 may deliver, e.g., using a pump, the drug or therapeutic agent at a constant or variable flow rate. IMD 22 may be programmable to adjust the number of doses, the frequency at which the doses are delivered, the amount of drug or therapeutic agent delivered per dose or the like. Drug pumps or drug delivery devices may be used to treat symptoms of a number of different conditions. For example, IMD 22 may deliver morphine or ziconotide to reduce or eliminate pain, baclofen to reduce or eliminate spasticity, chemotherapy to treat cancer, or any other drug or therapeutic agent to treat any other condition and/or symptom of a condition.

IMD 22 may include a reservoir (not shown) that may hold the drug or therapeutic agent. IMD 22 may be designed such that the reservoir holds a particular amount of the drug or therapeutic agent, such as a one-month supply. As such, patient 12 may have to schedule periodic device maintenance appointments to have the reservoir refilled with the drug or therapeutic agent used in the patient therapy. To this end, IMD includes a refill port 28 via which the reservoir (not shown) of IMD 22 may be filled or refilled. Refill port 28 may, for example, comprise a silicone rubber septum. To refill the reservoir of IMD 22, a physician or other user may identify the location of refill port 28, insert a needle of a syringe into refill port 28 and push the contents (i.e., drug or therapeutic agent) of the syringe through the needle into the reservoir via refill port 28.

Because IMD 22 is implanted within a patient, IMD 22 may include means for identifying the location of refill port 28. The means for identifying the location of refill port 28 may be referred to as a navigation system, navigation mechanism or the like. In one example, the navigation mechanism may include one or more sensors (e.g., pressure sensors) that detect when the needle is appropriately positioned within the refill port. This ensures that the physician injects the drug or therapeutic agent into the reservoir via refill port 28. IMD 22 may provide an indication that the physician has correctly identified refill port 28 in response to sensing pressure asserted by the needle. IMD 22 may, for example, send a signal to programmer 18. Alternatively, or additionally, IMD 22 may provide an audible alarm (such as a beep) to indicate that the needle has been correctly inserted into refill port 28. Other types of navigation mechanisms or system are also contemplated, such as detecting correct positioning of a template over IMD 22 or the like.

As described above with respect to FIG. 1, the user may also interact with programmer 18 to program IMD 22, e.g., select values for operational parameters of IMD 22. For drug delivery therapies, the user may use programmer 18 to select an amount of drug or therapeutic agent to deliver to patient 12, a rate (fixed or variable) at which the drug or therapeutic agent is delivered, or the like.

As in therapy system 10 of FIG. 1, the current demands on the power source of IMD 22 during wireless communication with programmer 18 may obstruct, impede or otherwise interfere with the ability of IMD 22 to perform other current intensive tasks, such as providing navigation to the physician or delivering therapies to patient 12. As such, a telemetry module of IMD 22 may operate in the duty cycled operational mode to free up the power source for non-telemetry functions, such as operating a pump to deliver the drug or therapeutic agent or navigation functions for refilling the reservoir of IMD 22, during peak power demands. In other instances, the telemetry module of IMD 22 may operate in the duty cycled operational mode when there is no competition for the resources of the power source of IMD 22, e.g., to reduce average current demands on the power source when IMD 22 is nearing end-of-service, to recharge a hold capacitor from which the telemetry module obtains power, to harvest energy or for any other reason.

Figure 3:
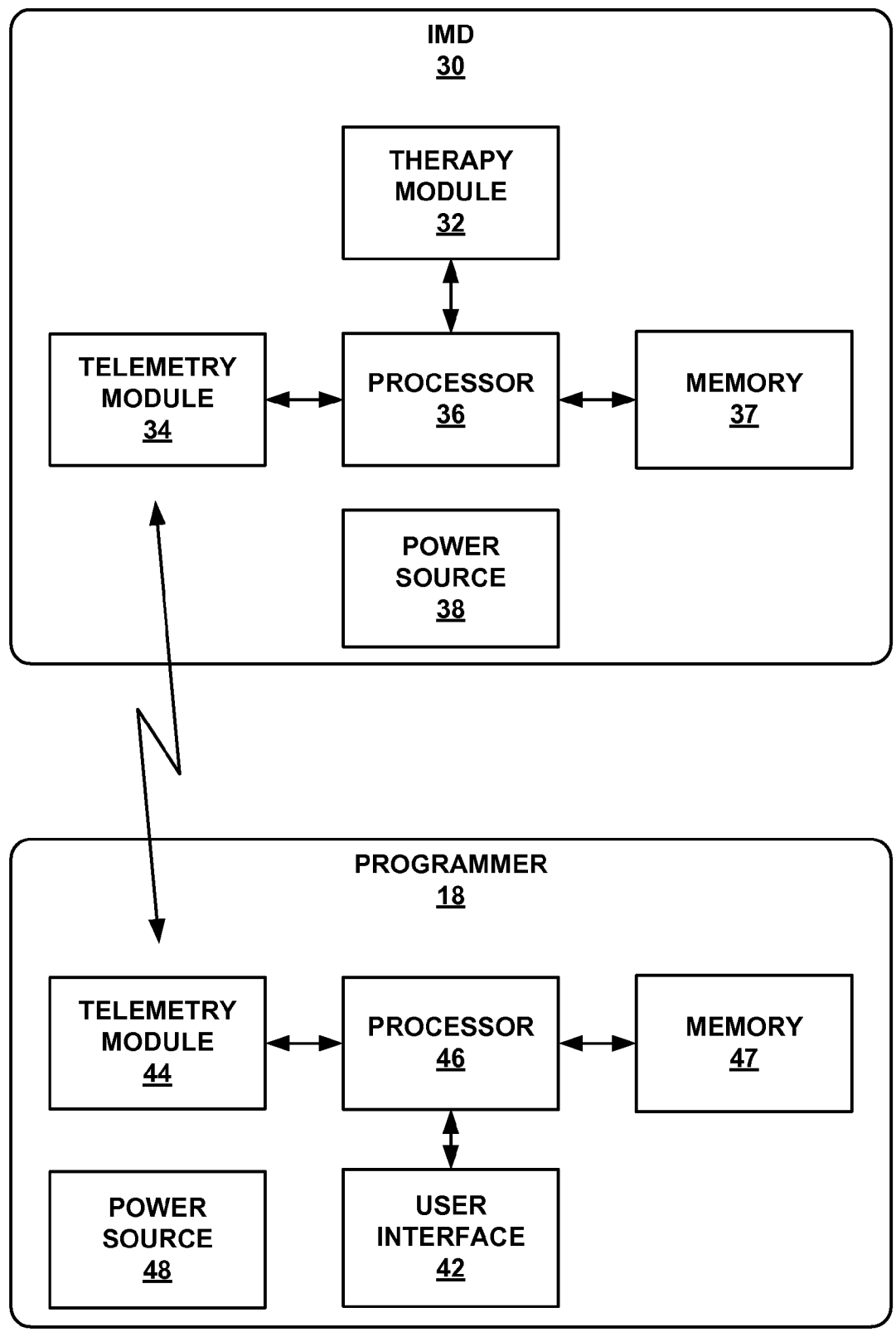
FIG. 3 is a block diagram illustrating an example implantable medical device (IMD) and programmer in further detail.

FIG. 3 is a block diagram illustrating an example IMD 30 and programmer 18 in further detail. IMD 30 may correspond to IMD 14 of FIG. 1, IMD 22 of FIG. 2 or another IMD. Likewise, programmer 18 may correspond to either of the programmers of FIG. 1 or 2, or a different programmer. As illustrated in FIG. 3, IMD 30 includes a therapy module 32, telemetry module 34, processor 36, memory 37 and power source 38. Programmer 18 includes a user interface 42, telemetry module 44, processor 46, memory 47 and power source 48.

As described above, a user may interact with programmer 18 to select therapy programs (e.g., sets of stimulation parameters), generate new therapy programs and/or modify therapy programs through individual or global adjustments. The user may interact with programmer 18 via user interface 42. User interface 42 may include, for example, a keypad and a display, which may be, for example, a cathode ray tube (CRT) display, a liquid crystal display (LCD) or light emitting diode (LED) display. The keypad may take the form of an alphanumeric keypad or a reduced set of keys associated with particular functions. Programmer 18 can additionally or alternatively include a peripheral pointing device, such as a mouse, via which a user may interact with the user interface. In some embodiments, the display of programmer 18 may include a touch screen display, and a user may interact with programmer 18 via the display.

Based on the therapy program selected by the user, processor 46 retrieves the parameters of the selected therapy program, which may be stored in memory 47. The parameters of the one or more selected therapy programs may be predetermined, input by the user, or a combination thereof. For example, a predetermined set of therapy programs may be stored within memory 47 for treating various conditions. In other instances, the selected therapy program may be input by the user and/or the user may modify the predetermined therapy programs to customize the program for patient 12.

The parameters of the therapy programs may include, for example, stimulation parameters (e.g., pulse amplitude, width and rate) in the case of electrical stimulation therapy or pump parameters (e.g., dosage and frequency/rate) for drug delivery therapies.

Processor 46 controls telemetry module 44 to transmit the parameters of the one or more selected therapy programs to IMD 30. Telemetry module 44 may communicate wirelessly with IMD 30 and, more specifically, with telemetry module 34 of IMD 30, e.g., using RF communications. As described above, in some instances, telemetry module 34 and 44 may communicate using MICS or MEDS. Telemetry module 44, under the control of processor 46, may also receive downlink data from IMD 30, which may include sensed physiological parameters, diagnosis generated based on the sensed physiological parameters, a log of delivered therapies, information regarding the amount of remaining battery power or the like.

Programmer 18 may establish a communication session with IMD 30 in accordance with the wireless communication technique utilized. Although the communication session may be established by either IMD 14 or programmer 18, typically the initiator of the session is programmer 18. Using MICS as an example, programmer 18 may initially listen to one or more of the ten channels of the MICS band to determine whether other users or noise exist on the channels. Programmer 18 may select the one of the channels that is not in use and has the least amount of noise. This process, sometimes referred to as "listen before talk," allows multiple simultaneous communication sessions to be collocated without interference. When operating in accordance with other protocols, such as MEDS, programmer 18 may not listen before talking.

Once programmer 18 identifies selects an available channel, programmer 18 establishes a communication session with IMD 30, e.g., using any of a variety of "handshake" mechanisms. Programmer 18 may, for example, transmit wakeup packets followed by open packets. IMD 30 may respond to the open packets and, once programmer 18 receives the open packets back from IMD 30, the communication session is established. Additionally, programmer 18 may send configuration information during the handshake process that specifies parameters of one or more duty cycled operational modes. Each of the duty cycled operational modes may correspond with different configuration events and/or different parameters, such as different duty cycle patterns or frequencies.

Telemetry module 44 may also be configured to communicate with another computing device (other than IMD 30) via wireless communication techniques, or direct communication through a wired connection. In some instances, programmer 18 may upload data retrieved from IMD 30 to a remote server, from which a clinician or another user may access the data to determine whether a potential sensing integrity issue exists or whether the measured physiological parameter values indicate patient 12 requires medical attention. An example of a remote server includes the CareLink® Network, available from Medtronic, Inc. of Minneapolis, Minn.

Examples of local wireless communication techniques that may be employed to facilitate communication between programmer 18 and another computing device include RF communication according to the 802.11 or BLUETOOTH specification sets, infrared communication, e.g., according to the IrDA standard, or other standard or proprietary telemetry protocols. In this manner, other external devices may be capable of communicating with programmer 18 without needing to establish a secure wireless connection.

Telemetry module 44 may include any suitable hardware, firmware, software or any combination thereof for communicating with IMD 30 and another computing device (e.g., remote server). For example, telemetry module 44 may include appropriate modulation, demodulation, frequency conversion, filtering, and amplifier components for transmission and reception of data, including radio frequency (RF) components and antennas, as applicable. In some instances, telemetry module 44 may include two or more sets of RF components, e.g., one for communication with IMD 30 and one for communication with another computing device.

Processor 46 may include one or more of a microprocessor, a controller, a digital signal processor (DSP), an application specific integrated circuit (ASIC), a field-programmable gate array (FPGA), or equivalent discrete or integrated logic circuitry. In some examples, processor 46 may include multiple components, such as any combination of one or more microprocessors, one or more controllers, one or more DSPs, one or more ASICs, or one or more FPGAs, as well as other discrete or integrated logic circuitry. The functions attributed to processor 46 herein may be embodied as software, firmware, hardware or any combination thereof.

Memory 47 includes computer-readable instructions that, when executed by processor 46, cause programmer 18 and processor 46 to perform various functions attributed to programmer 18 and processor 46 herein. Memory 47 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, magnetoresistive random access memory (MRAM), or any other digital media.

Power source 48 of programmer 18 delivers operating power to the components of programmer 18. Power source 48 may include a battery and a power generation circuit to produce the operating power for the components of programmer 18. In some examples, the battery may be rechargeable (e.g., nickel cadmium or lithium ion batteries) to allow extended operation. Recharging may be accomplished by electrically coupling power source 48 to a cradle or plug that is connected to an alternating current (AC) outlet. In addition or alternatively, recharging may be accomplished through proximal inductive interaction between an external charger and an inductive charging coil within programmer 18. In other embodiments, non-rechargeable batteries (e.g., non-rechargeable lithium based batteries such as lithium iodide) may be used. In addition, programmer 18 may be directly coupled to an AC outlet to power programmer 18. Power source 48 may include circuitry to monitor power remaining within a battery. In this manner, user interface 42 may provide a current battery level indicator or low battery level indicator when the battery needs to be replaced or recharged. In some cases, power source 48 may be capable of estimating the remaining time of operation using the current battery. Although the techniques of this disclosure are described primarily with respect to power source 38 being a battery, the techniques of this disclosure may be used in the context of other types of power sources. For example, power source 38 may be a power harvesting device that converts ambient energy into electrical energy, a capacitor or other mechanism for storing and delivering power.

IMD 30 may provide therapy, such as electrical stimulation therapy or drug delivery therapy, to patient 12 in accordance with the parameters of the one or more selected therapy programs received from programmer 18. In particular, processor 36 controls therapy module 32 to deliver therapy to patient 12 according to one or more therapy programs, which may be received from programmer 18 and stored in memory 37.

Processor 36 may include any one or more of a microprocessor, a controller, a DSP, an ASIC, a FPGA, or equivalent discrete or integrated logic circuitry. In some examples, processor 36 may include multiple components, such as any combination of one or more microprocessors, one or more controllers, one or more DSPs, one or more ASICs, or one or more FPGAs, as well as other discrete or integrated logic circuitry. The functions attributed to processor 36 herein may be embodied as software, firmware, hardware or any combination thereof.

Memory 37 includes computer-readable instructions that, when executed by processor 36, cause IMD 30 and processor 36 to perform various functions attributed to IMD 30 and processor 36 herein. Memory 37 may include any volatile, non-volatile, magnetic, optical, or electrical media, such as a RAM, ROM, NVRAM, EEPROM, flash memory, MRAM, or any other digital media.

In the case of electrical stimulation therapy, therapy module 32 may include a stimulation generator that generates and delivers electrical stimulation therapy, e.g., in the form of pulses or shocks. Processor 36 may control the stimulation generator to deliver electrical stimulation pulses with amplitudes, pulse widths, frequency, and/or electrode polarities specified by the one or more therapy programs. In the case of drug delivery therapy, therapy module 32 may include a pump that delivers a drug or therapeutic agent to patient 12. Processor 36 may control the pump to deliver the drug or therapeutic agent with the dosage and frequency (or rate) specified by the one or more therapy programs.

Processor 36 may also monitor signals sensed by one or more electrodes or other sensors coupled to therapy module 32 of IMD 30. These sensed signals may, in some instances, be stored within memory 37. For cardiac disease management therapy, for example, processor 36 may analyze electrical activity of the heart of patient 12, e.g., via sensed electrogram (EGM) or electrocardiogram (ECG) signals. Processor 36 may employ digital signal analysis techniques to characterize the signals to detect and classify the patient's heart rhythm from the sensed electrical signals. Processor 36 may also detect and classify the heart rhythm of patient 12 by employing any of the numerous signal processing methodologies known in the art. In this manner, processor 36 may detect arrhythmia episodes, such as tachycardia, bradycardia, fibrillation or other irregular heart rhythm. Processor 36 may analyze the sensed signals to detect a number of other conditions, such as a low blood sugar level, a high pH level, or any other condition and/or parameter.

Processor 36 may also control telemetry module 34 to receive downlink telemetry from and send uplink telemetry to programmer 18. Processor 36 may provide the data to be uplinked to programmer 18 and the control signals for telemetry circuitry within telemetry module 34, e.g., via an address/data bus. Telemetry module 34 transmits the data to programmer 18 in accordance with the control signals from processor 36. Telemetry module 34 may provide data received from programmer 18 (e.g., downlink data or downlink telemetry) to processor 36. Processor 36 may analyze the received data, store the received data within memory 37 and configure components of IMD 30, including therapy module 32 and telemetry module 34, in accordance with the received data.

Telemetry module 34 includes any suitable hardware, firmware, software or any combination thereof for communicating with another device, such as programmer 18 (FIGS. 1 and 2). For example, telemetry module 34 may include appropriate modulation, demodulation, frequency conversion, filtering, and amplifier components for transmission and reception of data, including radio frequency (RF) components and antennas, as applicable.

The various components of IMD 30 are coupled to power source 38, which may include a rechargeable or non-rechargeable battery. A non-rechargeable battery may be selected to last for several years, while a rechargeable battery may be inductively charged from an external charging device on a daily or weekly basis. In either case, and especially in the case of the non-rechargeable battery, the amount of power (sometimes referred to as "service life") of the battery is limited.

In the case of a non-rechargeable battery, for example, it is undesirable to replace the battery of IMD 30 as it typically requires a surgical procedure. As such, it is desirable to replace IMD 30 or the battery of IMD 30 as infrequently as possible. The techniques described in this disclosure may decrease peak current demands on power source 38 by multiplexing the use of power source 38 among the demanding components and/or functions. This, in turn, extends a service life of power source 38.

As described above, current drawn from power source 38 causes a voltage to drop due to the impedance of power source 38. As a result, the useful life of power source 38 may be reduced as the the voltage drop during a high rate current draw may be significant enough to render power source 38 incapable of supplying current at a desired rate. Power demand issues may therefore occur when more than one power intensive component of IMD 30 wants to perform functions simultaneously. To reduce power consumption and, in turn, extend service life of power source 38, the power multiplexing techniques of this disclosure may be used to reduce the rate at which current is drawn from power source 38.

In some instances, multiple components of IMD 30 and/or multiple functions of a single component may desire to operate concurrently. This may result in a peak current demand that exceeds current demands for which power source 38 is designed to handle. For example, telemetry module 34 may draw current from power source 38 to exchange communications with programmer 18 at the same time that other components of IMD 30 draw current from power source 38 to provide non-telemetry functions. In some instances, telemetry module 34 may draw current from power source 38 to communicate with programmer 18 at the same time therapy module 32 draws current from power source 38 to deliver therapy to patient 12. The power demands of telemetry module 34 may, in some instances, interfere with the ability of therapy module 32 to deliver therapy. For example, the power demands of telemetry module 34 may interfere with the ability of therapy module 32 to generate and deliver high demand pacing pulses. In other instances, telemetry module 34 may draw current from power source 38 to communicate with programmer 18 at the same time as another component of IMD 30 draws current from power source 38 to provide drug-pump refill navigation, possibly interfering with the navigation process.

In accordance with the techniques of this disclosure, telemetry module 34 of IMD 30 may operate in a "duty cycled operational mode" that includes one or more intervals during which a transceiver of telemetry module 34 is powered down interleaved with intervals during which the transceiver is powered up, e.g., for transmitting or receiving communications over the established communication session. During the intervals in which the transceiver of telemetry module 34 is powered down, telemetry module 34 may be drawing substantially less current than when in the powered up state. In other words, because the transceiver is powered down, the power demands of the telemetry module 34 are significantly reduced. A negligible amount of current may continue to be drawn from power source 38 to maintain information associated with the established communication session. The additional power, i.e., the power freed up by powering down the transceiver, may be used by other components of IMD 30 for performing other non-telemetry functions, such as therapy delivery functions or refill navigation functions. In other instances, the additional power freed up by powering down the transceiver may not be used by other components, thus conserving the current sourcing capability of power source 38, i.e., the capability to provide desired current rates. As such, telemetry module 34 may function in the duty cycled operational mode when power source 38 is nearing end-of-service (EOS).

The duty cycled operational mode described in this disclosure is different than conventional duty cycling of a transceiver. Duty cycling of a transceiver refers to a process in which the transceiver periodically wakes up from a powered down or "sleep" state to listen for a transmission from another device, e.g., programmer 18. When the transceiver detects a transmission from programmer 18, the transceiver transitions into an operational mode in which one or more communication sessions are established with programmer 18, e.g., in accordance with a medium access control (MAC) protocol by which network participants contend for access to the wireless medium. In this operational mode, the transceiver of IMD 30 exchanges communications with programmer 18. Conventionally, when in the operational mode, the transceiver transmits and receives communications without intervals in which the transceiver is powered down, which is referred to in this disclosure as the "normal" operational mode.

In the duty cycled operational mode described in this disclosure, telemetry module 30 is powered up and down at a particular rate such that one or more intervals during which a transceiver of telemetry module 34 is powered down are interleaved with intervals during which the transceiver is powered up. In contrast to conventional duty cycling of the transceiver, however, telemetry module 34 maintains information regarding the established session during the one or more intervals in which the transceiver is powered down. The current drawn from power source 38 to maintain the information regarding the established session is substantially less than in the powered up state and, in some instances, may be considered to be negligible. The information maintained during the intervals in which the transceiver of telemetry module 34 is powered down may include state and timing information such as channel number, packet timing, packet format, data rate or other state and/or timing information. Telemetry module 34 may therefore be viewed as continually being within an operational mode during the duty cycled operational mode.

The maintained state and timing information enables telemetry module 34 to immediately begin to transmit and receive information during the intervals in which the transceiver is powered up without renegotiating the communication channel with programmer 18. Instead, telemetry module 34 transmits and receives information on the previously established communication session. To the contrary, conventional duty cycling of the transceiver requires renegotiation of the transceiver when entering the operational mode. As such, conventional duty cycling of the transceiver is utilized in situations in which the transceiver can be powered down for long periods of times, e.g., minutes, hours or days. The duty cycled operational mode may be particularly useful in situations in which the transceiver is powered down for shorter periods of time, e.g., milliseconds or seconds.

The duty cycled operational mode is also different than the normal operational mode of the transceiver. As described above, when operating in a normal operational mode, transmit and receive functionality of telemetry module 34 is performed without intervals in which the transceiver is powered down. Instead, the transceiver is always powered on, even when the transceiver remains idle, i.e., is not transmitting or receiving information. On the other hand, the duty cycled operational mode of this disclosure includes intervals during which the transceiver is powered down interleaved with intervals during which the transceiver is powered up, e.g., for normal transmit and receive functionality.

In some instances, other components of IMD 30 may utilize the power source during the intervals in which the transceiver is powered down. For example, processor 36 may allocate the freed up power to another component, e.g., therapy delivery module 32, during at least a portion of the intervals during which the transceiver is powered down for generating and/or delivering an electrical stimulation, operating a pump to deliver a drug or therapeutic agent, operating one or more sensors or any other non-telemetry function. Processor 36 may also reallocate power from therapy delivery module 32 back to telemetry module 34 during the intervals in which the transceiver is powered up. In this manner, the duty cycled operational mode may be perceived as multiplexing the use of power source 38 among the various components and/or functions operating concurrently. As such, the duty cycled operational mode may be particularly useful during instances of high or peak current demand to reduce peak current demand on power source 38. In other instances, the additional power freed up by powering down the transceiver may not be used by other components, thus reducing average rate at which current is drawn from power source 38.

Processor 36 may configure telemetry module 34 in response to detecting a telemetry configuration event. In some instances, programmer 18 may transmit a communication or command to instruct IMD 30 to enter telemetry module 34 into the duty cycled operational mode. In this case, the communication may be the telemetry configuration event. Programmer 18 may send this command, for example, while establishing other parameters of the communication session, e.g., during the "handshake" process. Additionally, programmer 18 may send configuration information identifying configuration information related to the one or more duty cycled operational modes into which telemetry module 34 may enter. The specific one of the duty cycled operational modes into which telemetry module 34 enters may depend on the type of configuration event or functions IMD 30 is performing, as described in further detail below.

In response to the command, processor 36 of IMD 30 controls operation of telemetry module 34 to function in the duty cycled operational mode. The single command may, in some instances, cause IMD 30 to operate in the duty cycled operational mode until another command is received from programmer 18 instructing IMD 30 to enter the normal operational mode. As such, the single command from programmer 18 may result in introduction of a plurality of intervals in which telemetry module 34 is powered down. Alternatively, IMD 30 may enter the duty cycled operational mode in response to a command from programmer 18 and exit the duty cycled operational mode upon detecting the current level falling below a threshold value.

In other examples, the telemetry configuration event may occur within IMD 30. Thus, processor 36 of IMD 30 may configure telemetry module 34 to operate in the duty cycled operational mode without receiving a command from programmer 18. For example, processor 36 may monitor a current drawn from power source 38 and configure telemetry module 34 to operate in the duty cycled operational mode when the current drawn from power source 38 exceeds a peak threshold current. In this manner, the duty cycled operational mode may be used to reduce peak current demand as well as average current demand. As another example, processor 36 may monitor a power level of power source 38 and configure telemetry module 34 to operate in the duty cycled operational mode when the power level falls below a threshold power level. In this manner, the duty cycled operational mode may be used to reduce average power consumption when power source 38 is nearing end of service. In either case, processor 36 may send a communication to programmer 38 indicating that telemetry module 34 of IMD 30 is operating in the duty cycled operational mode.

While telemetry module 34 operates in the duty cycled operational mode, processor 46 of programmer 18 may control telemetry module 44 to also operate in the duty cycled operational mode to synchronize transmit and receive functionality of the telemetry modules. As such, the transceiver of telemetry module 44 may experience intervals in which it is powered down. These intervals would correspond with those of the transceiver of telemetry module 44. Alternatively, processor 46 may control telemetry module 44 to operate in a modified version of the duty cycled operational mode in which there are no intervals in which the transceiver of telemetry module 44 are powered down. Instead, processor 46 may control telemetry module 44 to transmit information during the intervals in which the transceiver of telemetry module 34 is powered down to ensure that the channel over which programmer 18 and IMD 30 communicate will not be usurped by another device.

As described above, processor 36 may control telemetry module 34 to enter into one of a plurality of different duty cycled operational modes. For example, a first duty cycled operational mode may be used when concurrently performing refill navigation and telemetry, and a second duty cycled operational mode may be used when concurrently performing refill navigation, therapy delivery and telemetry. Each of the duty cycled operational modes may vary in duty cycle frequency. For example, the first duty cycled mode may have a smaller duty cycle frequency than the second duty cycled operational mode. As another example, the intervals in which the telemetry module 34 is powered down may be longer in the second duty cycled mode as compared to the first duty cycled operational mode.

Additionally, processor 36 may control telemetry module 34 to transition between two different duty cycled operational modes having different duty cycle parameters. For example, processor 36 may control telemetry module 34 to enter a first duty cycled operational mode when refill navigation is performed concurrently with telemetry and control telemetry module 34 to operate in the second duty cycled operational mode when refill navigation is being performed in a device with a low battery (e.g., in a device near end of service) or when performing refill navigation concurrently with another high current function. As such, telemetry module 34 may not only transition between a normal operating mode and a duty cycled operational mode, but also between two duty cycled operation modes that correspond with different parameters (e.g., duty cycle frequencies or power down interval lengths).

Although the techniques of this disclosure are described primarily with respect to power demands of multiple components operating concurrently, the duty cycling techniques of this disclosure may be used other contexts in which there is no competition for the resources of power source 38 of IMD 30. For example, telemetry module 34 of IMD 30 may operate in accordance with the techniques of this disclosure in response to detecting that power source 38 is nearing end-of-service, thus reducing average current demands on power source 38 near end-of-service. As another example, telemetry module 34 of IMD 30 may obtain power from a hold capacitor (not shown) that hands off power source 38 and operate in accordance with the techniques of this disclosure to allow the capacitor to recharge. In other words, the hold capacitor is recharged during the power down states of telemetry module 34. As a further example, telemetry module 34 of IMD 14 may operate in accordance with the techniques of this disclosure to allow an energy harvesting device to harvest bursts of energy.

Although described in the context of a non-rechargeable power source, the duty cycled telemetry mode may be used in an IMD that operates on a rechargeable power source or an energy harvesting device. As such, the techniques of this disclosure may increase the amount of time between charges of the rechargeable power source or reduce power consumption when the rechargeable power source is approaching low power state, e.g., close to needing a recharge. As a further example, the telemetry module of IMD 14 may operate in accordance with the techniques of this disclosure to allow an energy harvesting device to harvest bursts of energy.

Figure 4A:
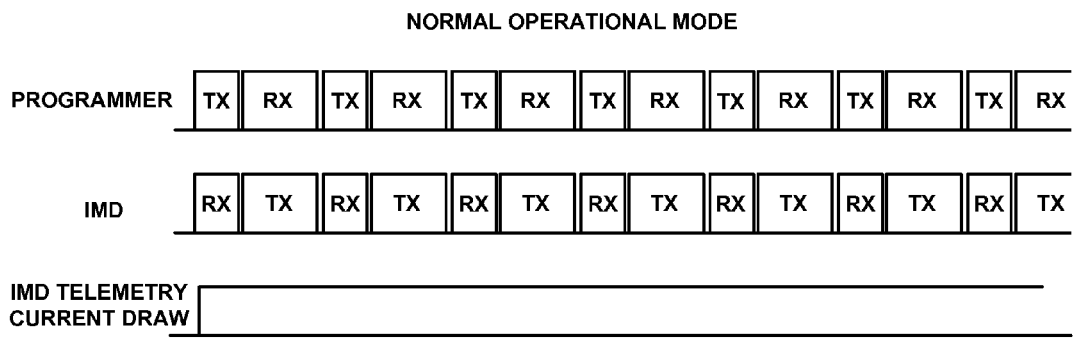
FIGS. 4A-4C are timing diagrams illustrating example operation of telemetry modules of a programmer and an IMD in a number of telemetry modes.
Figure 4B:
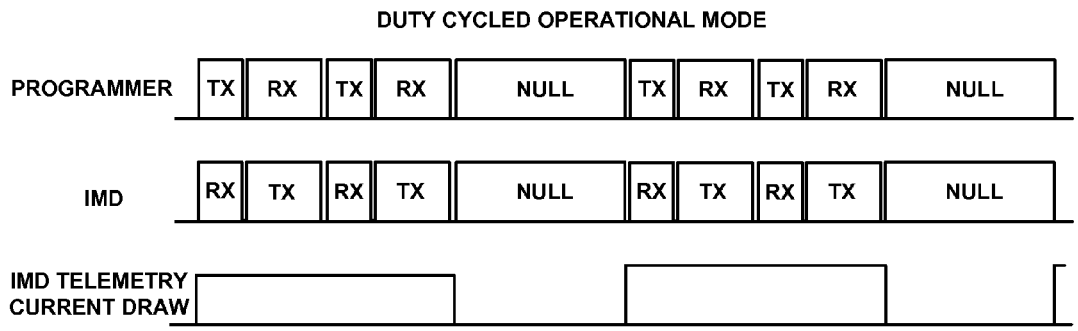
Figure 4C:
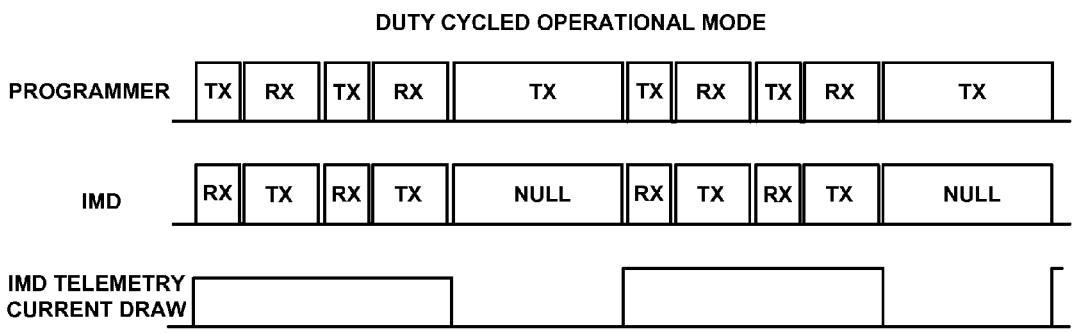

FIGS. 4A-4C are timing diagrams illustrating example operation of telemetry modules of a programmer and an IMD in a number of telemetry modes. The programmer may be any of programmers 18 of FIGS. 1-3 and the IMD may be any of IMDs 14, 22 and 30 of FIGS. 1-3. For purposes of description, however, the techniques will be described with respect to IMD 30.

FIG. 4A is a timing diagram illustrating example operation of programmer 18 and IMD 30 operating in a normal operational mode. In the normal operational mode, programmer 18 and IMD 30 include a plurality of consecutive transmit (TX) and receive (RX) operations. With reference to the timing diagram of programmer 18, for example, a transmit operation of programmer 18 is followed by a receive operation, followed by another transmit operation and another receive operation and so forth. The transmit and receive operations of IMD 30 are opposite of those of programmer 18. As shown in FIG. 4A, IMD 30 is receiving while programmer 18 is transmitting and IMD 30 is transmitting while programmer 18 is receiving.

The timing diagram labeled "IMD TELEMETRY POWER" represents the current drawn by the telemetry module of IMD 30 during the transmit and receive operations. As illustrated in FIG. 4A, the current drawn by the telemetry module of IMD 30 is a relatively constant level during the normal operational mode, such as approximately 10 milliamps (mA).

Although not illustrated in the example in FIG. 4A, one or more intervals or periods may exist in which the telemetry modules of IMD 30 or programmer 18 transitions to an idle state. While in the idle state, the transceiver remains powered up, but is neither transmitting nor receiving information. As such, the power demand of the transceiver during the idle state remains high.

FIGS. 4B and 4C are example timing diagrams illustrating two example implementations of the duty cycled operational mode. In the example illustrated in FIG. 4B, programmer 18 and IMD 30 include one or more intervals during which a transceiver of telemetry module 34 is powered down interleaved with intervals during which the transceiver is powered up, e.g., for transmitting or receiving communications over the established communication session. In the example illustrated in FIG. 4B both programmer 18 and IMD 30 include a plurality of intervals during which the transceiver is powered down, which occur at a periodic rate, e.g., after every N transmit and receive pairs. In other instances, the plurality of intervals during which the transceiver is powered down may occur at an irregular rate.

As illustrated in FIG. 4B, N=2, i.e., an interval during which the transceiver is powered down (labeled "NULL") occurs after two transmit and receive pairs. During the transmit and receive states or cycles (labeled "TX" and "RX," respectively), the transceiver is powered up. In other words, a transceiver of programmer 18 is powered up to transmit data for a period of time, receive data for a period of time, powers down for a period of time (e.g., during the periods labeled "NULL,") and then is powered up again transmit and receive data, powered down again for a period of time and so forth. Likewise, the transceiver of IMD 30 is powered up to receive data and transmit data, then is powered down for a period of time, then is powered up to transmit data and receive data and then is powered down for a period of time and so forth. These patterns are repeated while programmer 18 and IMD 30 are in the duty cycled operational mode.

Although the timing diagram illustrated in FIG. 4B includes two transmit and receive operations between the intervals in which the transceiver is powered down, more or fewer transmit and/or receive operations may be performed between the intervals in which the transceiver is powered down. For example, IMD 30 may perform three or more pairs of transmit and receive operations between each period of no (or negligible) transceiver action, i.e., TX-RX-TX-RX-TX-RX-NULL-TX-RX-TX-RX-TX-RX-NULL. As another example, IMD 30 may perform only one pair of transmit and receive operations between each period of no (or negligible) transceiver action, i.e., TX-RX-NULL-TX-RX-NULL. In other instances, intervals in which the transceiver is powered down may occur between each transmit and receive operation, i.e., TX-NULL-RX-NULL-TX-NULL-RX-NULL.

During the intervals in which the transceiver is powered down, the transceiver may continue to draw a negligible amount of current to enable telemetry module 34 to maintain information, e.g., state and timing information, regarding the previously established communication session or channel. The current drawn by telemetry module 34 to maintain the information regarding the established communication session may be less than approximately twenty percent of the current drawn by the telemetry module of IMD 30 during the normal operational mode and, more preferably less than ten percent. The amount of current that is drawn to maintain the information regarding the session is substantially less than the current drawn when the transceiver is powered up, and is therefore negligible.

The length of time of the interval during which the transceiver is powered down may vary based on the application and/or the peak power demand. The length of time of the interval during which the transceiver is powered down may, for instance, last for milliseconds or seconds. For example, the length of time of the interval during which the transceiver is powered down may be between approximately 1 and 100 milliseconds.

During the intervals in which the transceiver is powered down, other components of IMD 30 may utilize power source 38. In some instances, therapy module 32 may utilize power source 38 to generate and/or deliver a therapy during the intervals in which the transceiver is powered down. For example, therapy module 32 may use power source 38 to charge a capacitor to generate an electrical stimulation to deliver to patient 12. As another example, therapy module 32 may use power source 38 to operate a pump to dispense a drug or therapeutic agent to patient 12 during the intervals in which the transceiver is powered down. In this manner, IMD 30 may allocate the power of power source 38 among the various components and/or functions operating concurrently to reduce the peak current drain on the power source 38, in turn, extending a service life of power source 38. During intervals in which the transceiver is powered up, e.g., during the TX and RX states or cycles, IMD 30 may reallocate the power from one or more of the other components to the transceiver.

In other instances, no other components of IMD 30 may utilize power source during the period of time in which the transceiver is powered down. For example, the duty cycled operating mode reduces average current demands on power source 38. As another example, the duty cycled operational mode may allow a hold capacitor from which telemetry module 34 obtains power to recharge during the period of time in which the transceiver is powered down. As a further example, telemetry module 34 of IMD 30 may operate in the duty cycled operational mode to allow an energy harvesting device to harvest bursts of energy.

The timing diagram labeled "IMD TELEMETRY POWER" represents the current draw of telemetry module 34 of IMD 30 during the various cycles. As illustrated in FIG. 4B, the current drawn by telemetry module 34 of IMD 30 is "high" during the transmit and receive cycles and "low" during the NULL cycles. As such, the average current demand on power source 38 is reduced as there is little, if any, current drain on power source 38 by telemetry module 34 during the NULL cycles. In addition, during peak power demands, the peak current demand may also be reduced by allocating the power to other components during the intervals in which the transceiver is powered down. This may be particularly useful in scenarios in which the current demand on power source 38 exceeds a peak current demand for which power source 38 is designed. In some instances, processor 36 of IMD 30 may monitor the current demand of telemetry module 34, e.g., via a power monitoring pin of the transceiver, to determine when to allocate power source 38 to other components.

As described above, telemetry module 34 may continue to maintain information, e.g., state machines and/or timing information, regarding the established communication session during the intervals in which the transceiver is powered down. The maintained state and timing information enables telemetry module 34 to transmit and receive data during the TX and RX cycles without renegotiating the communication channel with programmer 18. Although telemetry module 34 is not completely powered-off during the non-telemetry cycles, the amount of power utilized to maintain the state and timing information is negligible (hence the "low" state) in comparison to the power demand when the transceiver is powered up.

FIG. 4C is a timing diagram illustrating another example implementation of the duty cycled operational mode. The example illustrated in FIG. 4C conforms substantially to that of FIG. 4B, except that programmer 18 transmits information during the intervals in which the transceiver is powered down. In other words, programmer 18 does not include intervals in which the transceiver is powered down. Instead, programmer 18 transmits information even though IMD 30 will not receive the information. In some instances, programmer 18 may transmit unintelligible information during the intervals in which the transceiver is powered down. In other instances, programmer 18 may retransmit a previously transmitted communication or a recently received communication during intervals in which the transceiver is powered down. By continuing to transmit information, the programmer will ensure that the channel over which programmer 18 and IMD 30 communicate, i.e., the channel selected during the initialization of the communication session, will not be usurped by another device. The technique illustrated in FIG. 4C may be particularly effective when the intervals in which the transceiver is powered down are longer than an amount of time another device is required to monitor each channel to determine whether it is in use. In the case of the MICS band, the technique illustrated in FIG. 4C may be particularly effective when the intervals in which the transceiver is powered down are longer than 10 milliseconds.

Figure 5:
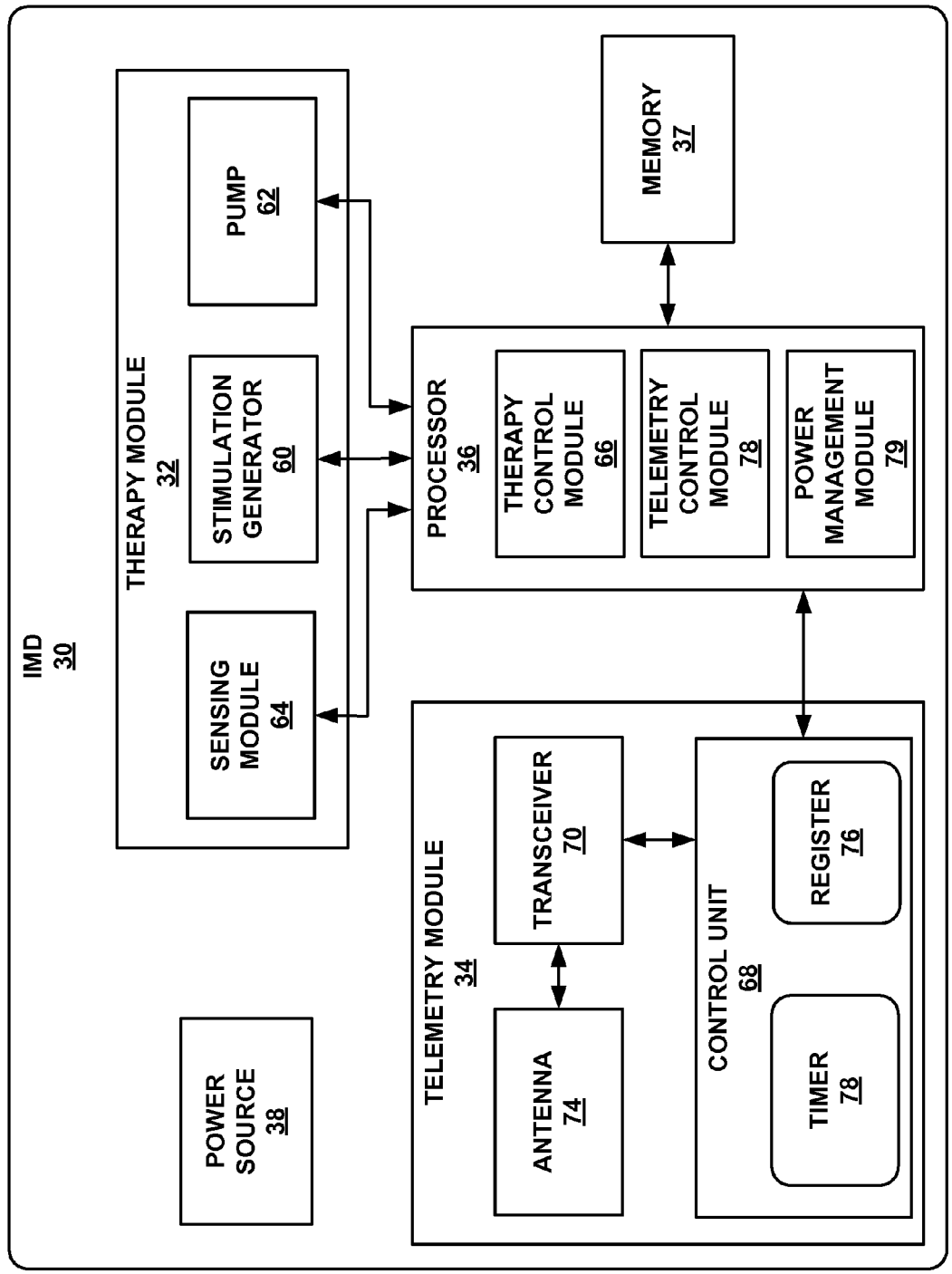
FIG. 5 is a block diagram illustrating the IMD of FIG. 3 in further detail.

FIG. 5 is a block diagram illustrating IMD 30 of FIG. 3 in further detail. As described above with respect to FIG. 3, therapy module 32 of IMD 30 provides therapy to patient 12. To this end, therapy module 32 may include at least one stimulation generator 60 that generates and delivers an electrical stimulation via one or more electrodes on a lead coupled to stimulation generator 60. Alternatively or additionally, therapy module 32 may include at least one pump that delivers a drug or therapeutic agent to patient 12 via a catheter to which the pump is coupled.

Therapy module 32 may also include a sensing module 64 that receives signals from one or more sensing electrodes or other sensors to which sensing module 64 is coupled. Therapy module 32 may be coupled to the sensing electrodes or other sensors via a wired coupling or wirelessly. In one instance, sensing module 64 may be coupled to one or more sensing electrodes of a lead and sense one or more physiological parameters of patient 12, such as electrical signals attendant to depolarizations and repolarizations of the heart, neurologic parameters, intracardiac or intravascular pressure, activity, posture, pH of blood or other bodily fluids or the like. In other instances, sensing module 64 may be coupled to one or more sensors (e.g., pressure sensors) for use in identifying a location of the implanted medical device. For example, sensing module 64 may receive signals from one or more pressure sensors that indicate a physician has correctly identified the location of IMD 30 or a particular port of IMD 30, such as a refill port 28 (FIG. 2).

The therapy provided by therapy module 32 may be controlled by processor 36. In particular, a therapy control module 66 of processor 36 may control therapy module 32 and, more specifically, stimulation generator 60 and/or pump 62 to deliver therapy to patient 12 according to one or more therapy programs, which may be stored in memory 37. Therapy control module 66 may control stimulation generator 60 to deliver electrical stimulation pulses with amplitudes, pulse widths, frequency, and/or electrode polarities specified by the one or more therapy programs. Additionally, therapy control module 66 may control pump 62 to deliver a drug or therapeutic agent with the dosage and frequency (or rate) specified by the one or more therapy programs. In some instances, therapy control module 66 may adjust the therapy based on sensed signals, e.g., one or more sensed physiological parameters.

Telemetry module 34 of FIG. 5 includes a control unit 68, a transceiver 70 and an antenna 74. Transceiver 70 may include suitable components for communicating with programmer 18, such as one or more amplifiers, mixers, modulators, demodulators, analog-to-digital converters (ADCs), digital-to-analog converters (DACs), filters and the like. Transceiver 70 may include circuitry for both receiving and transmitting communications. In other instances, telemetry module 34 may include separate transmitter and receiver components instead of transceiver 70. Transceiver 70 transmits and receives signals via at least one antenna 74. Antenna 74 may be internal and/or external to a housing of IMD 30. Additionally, in some instances, IMD 30 may include more than one antenna.

Control unit 68 may maintain information regarding an established communication session with programmer 18. In the example illustrated in FIG. 1, control unit 68 includes a register 76 and timer 78. Register 76 may, for example, maintain state information that indicates to control unit 68 the state of the next frame or cycle. In one instance, the state of the next frame or cycle may be a transmit frame/cycle, a receive frame/cycle or a null frame/cycle. Control unit 68 may configure transceiver 70 in accordance with the state indicated in register 76, e.g., switch between transmit and receive, power up or power down transceiver, or the like. Timer 78 may track the amount of time that has elapsed for the current state to allow control unit 68 to determine when to switch to the next state.

Telemetry module 34 may operate to receive downlink telemetry from and send uplink telemetry to programmer 18 under the control of processor 36 and, more specifically, telemetry control module 78 of processor 36. For example, telemetry control module 78 may provide control signals for telemetry circuitry within telemetry module 34, e.g., via an address/data bus. The control signals include, for example, the next frame state written to register 76 and/or a timer value for timer 78. Table 1 provides an example of control signals and associated states.

TABLE 1

| Control signal and associated states | |
|---|---|
| Control signal | State |
| 000 | IDLE |
| 001 | TX |
| 010 | TX NULL |
| 101 | RX |
| 110 | RX NULL |
| OTHER | IDLE |

In Table 1, the control signal from telemetry control module 78 is a three bit control signal. When the control signal is 000 control unit 68 configures telemetry module 34 to operate in an IDLE state in which the transceiver (transmit and receive circuitry) is powered up, but the transceiver is neither transmitting nor receiving data. When the control signal is 001 or 101, control unit 68 configures telemetry module 34 to operate in an TX state or RX state, respectively, in which the transceiver performs the respective transmit or receive operation. The transceiver is powered up during both the TX and RX states. When the control signal is 010 or 110, control unit 68 configures telemetry module 34 to power down the transmit and/or receive circuitry to operate in a TX NULL or RX NULL state, respectively. Separate NULL signals may exist for TX and RX because the transmit and receive timing may be of a different duration. If the control signal takes on any other value, control unit 68 configures telemetry module 34 to operate in the IDLE state.

Telemetry module 34 transmits the data to and receives data from programmer 18 in accordance with the control signals from telemetry control module 78. Telemetry control module 78 may control telemetry module 34 in accordance with a telemetry mode specified by programmer 18. For example, programmer 18 may transmit a communication to IMD 30 instructing that telemetry control module 78 configure telemetry module 34 to initially operate in accordance with the duty cycled operational mode or switch from a normal operational mode to the duty cycled operational mode.

Depending on the demand on power source 38 or in response to a command from programmer 18, telemetry control module 78 may reconfigure telemetry module 34 from the duty cycled telemetry mode to a normal telemetry mode. As described above, the normal telemetry mode does not include intervals during which the transceiver is powered down. Moreover, in the normal telemetry mode, telemetry module 34 continues to communicate over the previously established communication session.

A power management module 79 of processor 36 may monitor a load (e.g., current) demand of power source 38. When the current demand of power source 38 falls below a threshold level for a particular duration of time, telemetry control module 78 may control telemetry module 34 to operate in the normal telemetry mode, e.g., by providing commands to register 76. In this manner, telemetry module 34 may be reconfigured to operate in the normal operational mode in response to a monitored condition of power source 38. Telemetry control module 78 may also control telemetry module 34 to transmit a communication to programmer 18 to indicate that telemetry control module 78 is now operating in the normal telemetry mode. Telemetry control module 78 may transition back to the duty cycled control mode, if the power demand rises again or in response to another command from programmer 18. In other instances, programmer 18 may interrogate IMD 30 to obtain the current demand or other load information, detect high current demand conditions and program telemetry module 34 into the duty cycled operational mode, e.g., in response to a command from programmer 18.

In other instances, telemetry control module 78 may control telemetry module 34 in accordance with a telemetry mode selected based on a level of power source 38. For example, when power source 38 is a battery, telemetry control module 78 may control telemetry module 34 to operate in the duty cycled operational mode in response to the power source 38 falling below a particular threshold power level. In this manner, telemetry control module 78 may operate in the duty cycled operational mode when the battery is approaching end of service. In some instances, telemetry control module 78 may operate in the duty cycled operational mode for a substantial amount of time or all the time to reduce the average current draw of telemetry module 34.

Control unit 68 may comprise one or more of a microprocessor, a controller, a DSP, an ASIC, a FPGA, or equivalent discrete or integrated logic circuitry. In some examples, control unit 68 may include multiple components, such as any combination of one or more microprocessors, one or more controllers, one or more DSPs, one or more ASICs, or one or more FPGAs, as well as other discrete or integrated logic circuitry. As such, in some instances, control unit 68 may control the operation of telemetry module 34 instead of telemetry control module 78 of processor 36. In this case, the functions attributed to telemetry control module 78 may be performed by control unit 68.

Processor 36 of IMD 30 may monitor the power demand of telemetry module 34, e.g., via a power monitoring pin of the transceiver to determine when transceiver 70 is powered up and powered down. During intervals in which transceiver 70 is powered down, power management module 79 of processor 36 may allocate power source 38 to other components, such as therapy module 32. During intervals in which transceiver 70 is powered up, power management module 79 of processor 36 may reallocate power of power source 38 from other components to transceiver 70. In this manner, power management module 79 may be perceived as multiplexing the use of the power source among the various components. This may be particularly useful during peak power demands when competition for the limited power of the power source is greatest.

Figure 6:
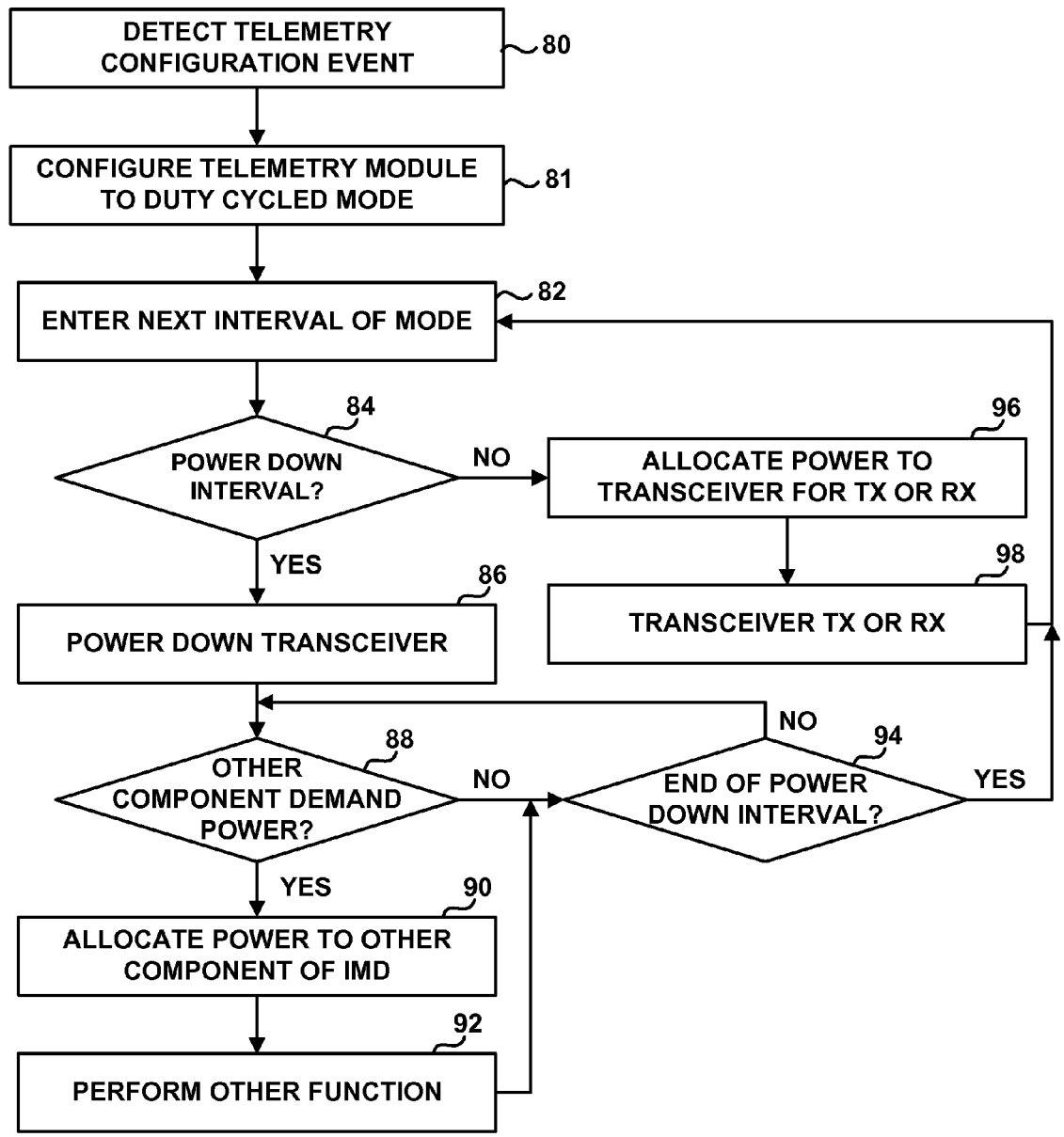
FIG. 6 is a flow diagram illustrating example operation of an IMD operating in accordance with a duty cycled operational mode.

FIG. 6 is a flow diagram illustrating example operation of an IMD, such as IMD 30, operating in accordance with a duty cycled operational mode. Although FIG. 6 is described with reference to IMD 30, other devices may operate in accordance with the duty cycled operational mode. For example, in some instances, a programmer 18 may operate in substantially the same manner as described with respect to IMD 30.

Initially, processor 36 of IMD 30 may detect a telemetry configuration event (80). The telemetry configuration event may, for example, be reception of a communication or command from programmer 18 instructing processor 36 to configure telemetry module 34 to operate in the duty cycled operational mode. In other instances, the telemetry configuration event may be a condition detected within IMD 30, such as a current drawn from power source 38 exceeding a peak threshold current or a power level of power source 38 falling below a threshold power level.

In any case, processor 36 configures the telemetry module to operate in a duty cycled operational mode in response to the telemetry configuration event (81). As described in detail in this disclosure, the duty cycled operational mode includes one or more intervals during which transceiver 70 is powered down interleaved with intervals during which transceiver 70 is powered up, e.g., for transmitting and/or receiving communications over an established communication session. Moreover, in the duty cycled telemetry mode, telemetry module 34 maintains information regarding the established communication session during the intervals in which the transceiver is powered down.

While operating in the duty cycled operational mode, telemetry module 34 enters a next interval of the mode (82). The next interval may be either a powered down interval or a powered up interval (e.g., a transmit, receive or idle state). Processor 36 determines whether the interval is a power down interval (84). If the interval is a power down interval ("YES" branch of block 84), processor 36 powers down transceiver 70 (86).

Processor 36 determines whether any other components of IMD 30 demand power (88). When any of the other components of IMD 30 demand power ("YES" branch of block 88), power management module allocates the power freed up by powering down transceiver 70 to the other component of IMD 30 (90). The other component of IMD 30 performs one or more other functions, such as delivering therapy to patient 12 (92).

When there are no other components of IMD 30 that desire power ("NO" branch of block 88) or after performing all or a portion of the other functions, processor 36 determines whether an end of the power down intervals has been reached (94). When the end of the power down interval has not been reached ("NO" branch of block 94), processor 36 continues to determine whether there are other components that desire power and, if so, allocate power to those components.

When the end of the power down interval has been reached ("YES" branch of block 94), telemetry module 34 enters a next interval of the duty cycled operational mode. When the current interval of the duty cycled operation mode is not a power down interval, processor 36 continues to allocate and/or reallocates power to power up transceiver for performing transmit and/or receive operations (96). Transceiver 70 transmits and/or receives communications via the previously established communication session (98).

Although FIG. 6 is described primarily with respect to power demands of multiple components operating concurrently, the duty cycled operational mode may be used other contexts in which there is no competition for the resources of the power source of IMD 14. In these instances, after the transceiver is powered down (block 86), processor 36 of IMD 30 may not allocate the power source to other components of IMD 30. Instead, no other component of IMD 30 may utilize the freed up power, thus reducing average current demands on the power source when IMD 30 is nearing end-of-service. As another example, telemetry module 34 of IMD 30 may obtain power from a hold capacitor that is coupled to power source 38 and the capacitor may be recharged during the powered down state.

Figure 7:
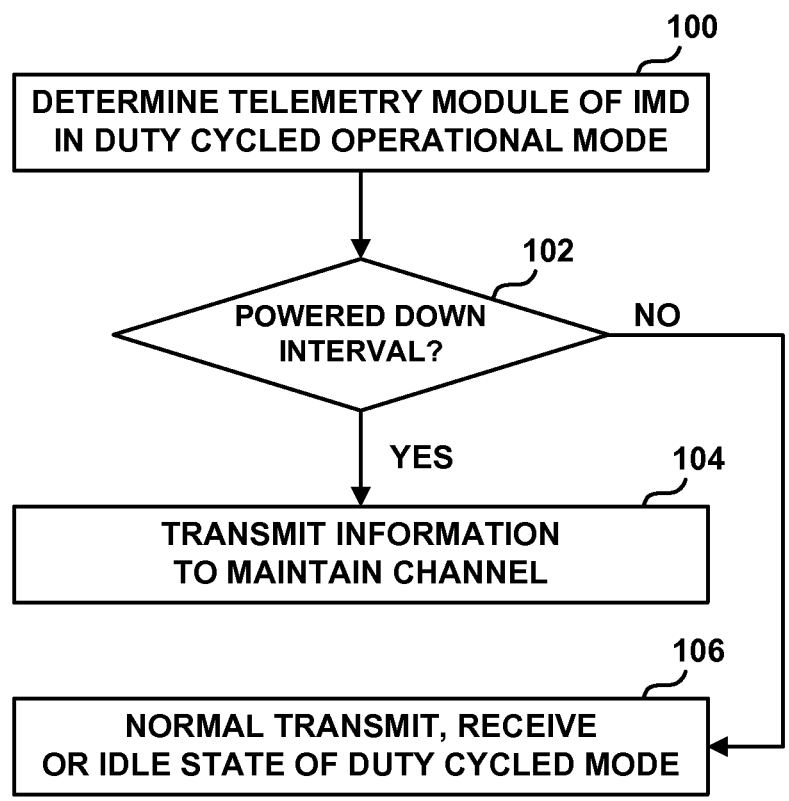
FIG. 7 is a flow diagram illustrating an example operation of a programming device operating in a modified duty cycled operational mode.

FIG. 7 is a flow diagram illustrating an example operation of a programming device, such as programmer 18, operating in a modified duty cycled operational mode. Programmer 18 determines that a telemetry module of IMD 30 is operating in a duty cycled operational mode that includes at least one interval during which a transceiver of the telemetry module is powered down interleaved with intervals during which the transceiver is powered up for transmitting or receiving communications over an established communication session (100). In instances in which programmer 18 configures the telemetry module of IMD 30, programmer 18 may determine that the telemetry module of IMD 30 operates in the duty cycled operational mode based on the commands sent to IMD 30. In instances in which IMD 30 configures its telemetry module, programmer 18 may receive a communication indicating that the telemetry module of IMD 30 is operating in the duty cycled operational mode.

Programmer 18 may determine whether the current state of the telemetry module of IMD 30 is in a power down interval (102). Programmer 18 may determine that current state of the telemetry module of IMD 30 is in a power down interval based on state and timing information regarding the communication session. When programmer 18 determines that the transceiver of IMD 30 is powered down ("YES" branch of block 102), programmer 18 may transmit information to maintain the established communication session (104). The information transmitted by programmer 18 may be unintelligible information, information transmitted during a previous transmit cycle or any other information.

When programmer 18 determines that the transceiver of IMD 30 is not currently powered down ("NO" branch of block 102), programmer 18 may function in accordance with the normal transmit, receive or idle state of the modified duty cycled operational mode (106).

The techniques described in this disclosure may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A system comprising:
an implantable medical device that includes a telemetry module configured to operate in a duty cycled operational mode that includes at least one interval during which a transceiver of the telemetry module is powered down interleaved with intervals during which the transceiver is powered up for transmitting or receiving communications over an established communication session, wherein the telemetry module maintains information regarding the established communication session during the at least one interval in which the transceiver is powered down; and
a programming device that communicates with the implantable medical device, wherein the programming device establishes a communication session with the implantable medical device and, during the established communication session, determines that the telemetry module of the implantable medical device is operating in a duty cycled operational mode, and transmits information during the at least one interval in which the transceiver of the implantable medical device is powered down during the duty cycled operational mode.

2. The system of claim 1, wherein
the programming device transmits a communication to the implantable medical device instructing the implantable medical device to configure the telemetry module to operate in the duty cycled operational mode; and
the implantable medical device configures the telemetry module to operate in the duty cycled telemetry mode in response to the communication.

3. The system of claim 1, wherein the implantable medical device monitors performance of a power source of the implantable medical device and configures the telemetry module to operate in the duty cycled operational mode in response to detecting one of a level of the power source falling below a threshold power level and a current drawn from the power source exceeding a peak threshold current.

4. The system of claim 3, wherein the implantable medical device transmits a communication to the programming device indicating that the telemetry module of the implantable medical device is operating in the duty cycled operational mode.

5. The system of claim 1, wherein
the telemetry module comprises a first component, and
the implantable medical device further comprises at least one other component, the implantable medical device allocating power from a power source of the implantable medical device to the at least one other component during the at least one interval in which the transceiver is powered down.

6. The system of claim 5, wherein the at least one other component comprises a therapy delivery module.

7. The system of claim 5, wherein the implantable medical device allocates the power from the power source to perform at least one of generating an electrical stimulation, delivering an electrical stimulation, operating a pump to deliver a drug or therapeutic agent, and operating one or more sensing components.

8. The system of claim 5, wherein the implantable medical device reallocates power from the at least one other component to the telemetry module during the intervals in which the transceiver is powered up for transmitting or receiving communications over the established communication session.

9. The system of claim 1, wherein the implantable medical device reconfigures the telemetry module from the duty cycled operational mode to an operational mode that does not include intervals during which the transceiver is powered down and communicates over the previously established communication session in accordance with the second operational mode.

10. The system of claim 1, wherein the implantable medical device reconfigures the telemetry module in response to one of a communication from the programming device and a monitored condition of a power source of the implantable medical device.

11. The system of claim 1, wherein the at least one interval during which the transceiver is powered down comprises a plurality of intervals that occur at a periodic rate.

12. The system of claim 1, wherein the programming device transmits one of unintelligible information and a previously transmitted communication during the at least one interval in which the transceiver of the implantable medical device is powered down.

13. The system of claim 1, wherein:
the implantable medical device does not receive the information transmitted by the programming device during the at least one interval in which the transceiver is powered down;
the programming device transmits information during the at least one interval in which the transceiver is powered up; and
the implantable medical device receives the information transmitted by the programming device during the at least one interval in which the transceiver is powered up.

14. The system of claim 1, wherein the programming device and the implantable medical device communicate in accordance with one of the Medical Implant Communications Service (MICS) band regulation or the Medical External Data Service (MEDS) band regulation.

15. A programming device comprising:
a telemetry module that exchanges communications with an implantable medical device; and
a processor that controls operation of the telemetry module, wherein the processor:
establishes a communication session with the implantable medical device;
determines that a transceiver of the implantable medical device is operating in a duty cycled operational mode during the established communication session, wherein the duty cycled operational mode includes at least one interval during which the transceiver of the implantable medical device telemetry module is powered down interleaved with intervals during which the transceiver of the implantable medical device is powered up for transmitting or receiving communications over the established communication session, and
controls the telemetry module to transmit information during the at least one interval in which the transceiver of the implantable medical device is powered down.

16. The device of claim 15, wherein the processor controls the telemetry module to transmit a communication to the implantable medical device instructing the implantable medical device to configure the transceiver of the implantable medical device to operate in the duty cycled operational mode.

17. The device of claim 15, wherein the processor receives a communication from the implantable medical device via the telemetry module, the communication indicating that the transceiver of the implantable medical device is operating in the duty cycled operational mode.

18. The device of claim 15, wherein the processor controls the telemetry module to transmit a communication to the implantable medical device instructing the implantable medical device to reconfigure the transceiver of the implantable medical device from operating in the duty cycled operational mode to an operational mode that does not include intervals during which the transceiver is powered down.

19. The device of claim 15, wherein the programming device transmits one of unintelligible information and a previously transmitted communication during the at least one interval in which the transceiver of the implantable medical device is powered down.

20. The device of claim 15, wherein the programming device operates in accordance with one of the Medical Implant Communications Service (MICS) band regulation or the Medical External Data Service (MEDS) band regulation.

21. A method comprising:
establishing a communication session with an implantable medical device;
determining that a transceiver of the implantable medical device is operating in a duty cycled operational mode during the established communication session, wherein the duty cycled operational mode that includes at least one interval during which the transceiver of the implantable medical device is powered down interleaved with intervals during which the transceiver of the implantable medical device is powered up for transmitting or receiving communications over the established communication session, and
transmitting information during the at least one interval in which the transceiver of the implantable medical device is powered down.

22. The method of claim 21, further comprising transmitting a communication to the implantable medical device instructing the implantable medical device to configure the transceiver of the implantable medical device to operate in the duty cycled operational mode.

23. The method of claim 21, determining that the transceiver of an implantable medical device is operating in the duty cycled operational mode comprises receiving a communication from the implantable medical device indicating that the transceiver of the implantable medical device is operating in the duty cycled operational mode.

24. The method of claim 21, further comprising transmitting a communication to the implantable medical device instructing the implantable medical device to reconfigure the transceiver from the duty cycled operational mode to an operational mode that does not include any intervals during which the transceiver of the implantable medical device is powered down.

25. The method of claim 21, wherein transmitting information during the at least one interval in which the transceiver of the implantable medical device is powered down comprises transmitting one of unintelligible information and a previously transmitted communication during the at least one interval in which the transceiver of the implantable medical device is powered down.

26. A device comprising:
means for establishing a communication session with an implantable medical device;
means for determining that a transceiver of the implantable medical device is operating in a duty cycled operational mode during the established communication session, wherein the duty cycled operational mode includes at least one interval during which the transceiver of the implantable medical device is powered down interleaved with intervals during which the transceiver of the implantable medical device is powered up for transmitting or receiving communications over the established communication session, and
means for transmitting information during the at least one interval in which the transceiver of the implantable medical device is powered down.

27. The device of claim 26, wherein
the transmitting means transmit a communication to the implantable medical device instructing the implantable medical device to configure the transceiver of the implantable medical device to operate in the duty cycled operational mode; and
the determining means determine that the transceiver of an implantable medical device is operating in the duty cycled operational mode in response to transmitting the communication.

28. The device of claim 26, wherein the determining means determine that the transceiver of an implantable medical device is operating in the duty cycled operational mode in response to receiving a communication from the implantable medical device indicating that the transceiver of the implantable medical device is operating in the duty cycled operational mode.

29. The device of claim 26, wherein the transmitting means transmit a communication to the implantable medical device instructing the implantable medical device to reconfigure the transceiver from the duty cycled operational mode to an operational mode that does not include any intervals during which the transceiver is powered down.

30. The device of claim 26, wherein the transmitting means transmit one of unintelligible information and a previously transmitted communication during the at least one interval in which the transceiver of the implantable medical device is powered down.

31. The device of claim 26, wherein the device operates in accordance with one of the Medical Implant Communications Service (MICS) band regulation or the Medical External Data Service (MEDS) band regulation.

32. A computer-readable medium comprising instructions that when executed cause a device to:
establish a communication session with an implantable medical device;
determine that a transceiver of the implantable medical device is operating in a duty cycled operational mode during the established communication session, wherein the duty cycled operational mode includes at least one interval during which the transceiver of the implantable medical device is powered down interleaved with intervals during which the transceiver of the implantable medical device is powered up for transmitting or receiving communications over the established communication session, and
transmit information during the at least one interval in which the transceiver of the implantable medical device is powered down.

33. The computer-readable medium of claim 32, wherein instructions to transmit information comprise instructions to transmit one of unintelligible information and a previously transmitted communication during the at least one interval in which the transceiver of the implantable medical device is powered down.

* * * * *